United States Patent [19]

Yarger

[11] Patent Number: 5,674,209

[45] Date of Patent: Oct. 7, 1997

[54] CONNECTOR FOR ATTACHMENT TO A DRAIN TUBE

[76] Inventor: Richard J. Yarger, 4908 Douglas Dr., Yakima, Wash. 98908

[21] Appl. No.: 589,529

[22] Filed: Jan. 22, 1996

[51] Int. Cl.⁶ .................................................. A61M 25/00
[52] U.S. Cl. .................. 604/283; 604/256; 604/905; 285/901; 128/912
[58] Field of Search ................... 604/27, 30, 167, 604/169, 246, 256, 264, 283, 284, 322, 327, 905; 128/912, DIG. 26; 215/200, 204; 285/332, 901

[56] References Cited

U.S. PATENT DOCUMENTS

| 3,058,472 | 10/1962 | Thornton, Jr. . | |
|---|---|---|---|
| 4,349,024 | 9/1982 | Ralston, Jr. | 604/905 |
| 4,611,785 | 9/1986 | Steer | 604/256 |
| 4,863,438 | 9/1989 | Gauderer et al. . | |
| 4,944,732 | 7/1990 | Russo . | |
| 5,125,897 | 6/1992 | Quinn et al. . | |
| 5,263,944 | 11/1993 | Vidal et al. . | |
| 5,267,983 | 12/1993 | Oilschlager et al. . | |
| 5,290,250 | 3/1994 | Bommarito . | |
| 5,295,599 | 3/1994 | Smith | 215/204 |
| 5,360,414 | 11/1994 | Yarger . | |
| 5,382,242 | 1/1995 | Horton et al. | 604/283 |
| 5,413,561 | 5/1995 | Fischell et al. | 604/256 |
| 5,507,535 | 4/1996 | McKamey et al. | 604/283 |

*Primary Examiner*—Mark Bockelman
*Assistant Examiner*—Bhisma Mehta
*Attorney, Agent, or Firm*—Christensen O'Connor Johnson & Kindness PLLC

[57] ABSTRACT

The connector includes a socket (14) attachable to the proximal end of the drain tube so that the socket is in fluid flow communication with the drain tube. An adapter (38) having opposite tapered ends is provided for connecting the socket to the suction/collection device. The adapter is flexibly connected to the socket to be movable between first and second positions. In the first position, one end of the adapter is inserted into the socket. In the second position, both ends are removed from the socket. A cap (22) is flexibly connected to the socket for substantially closing-off the socket. The cap may cover one end of the adapter while the other end of the adapter is inserted in the socket, or the cap may be inserted directly into the socket.

13 Claims, 1 Drawing Sheet

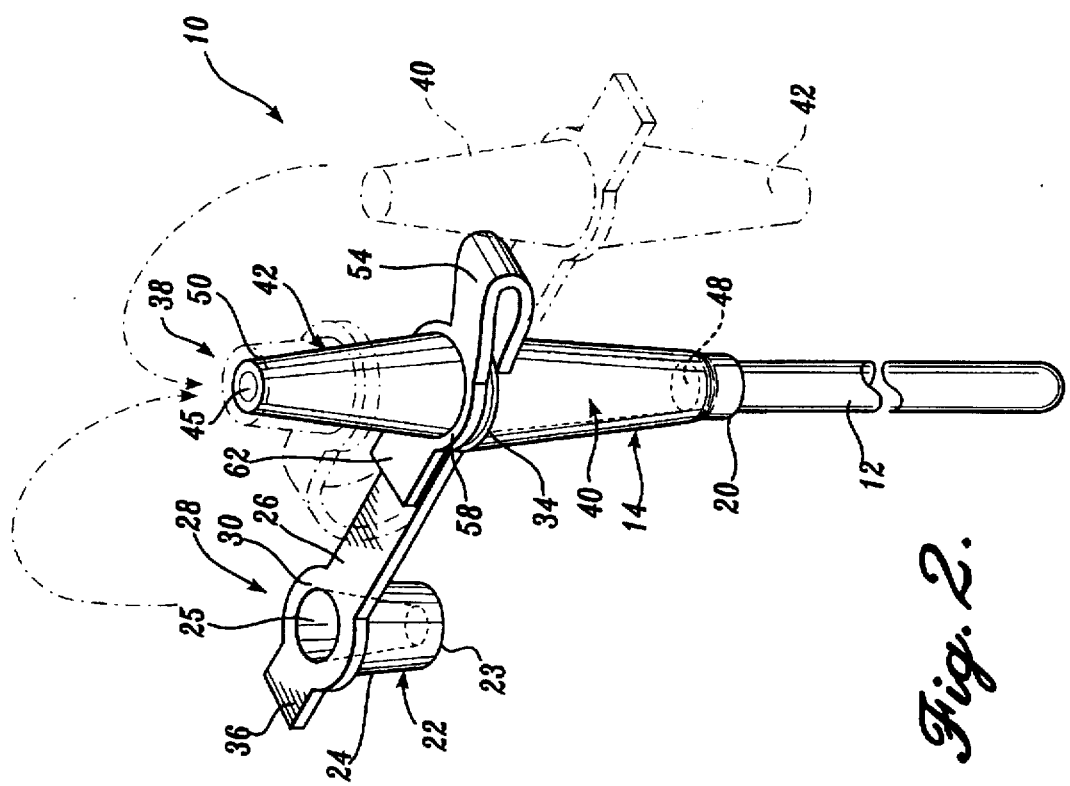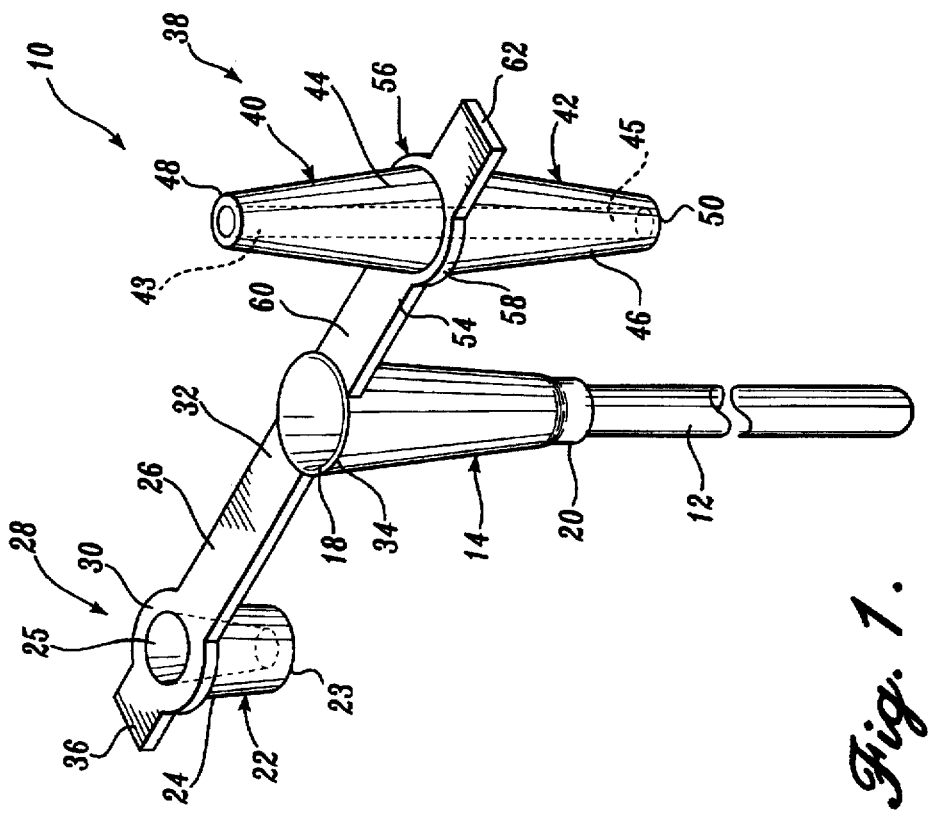

CONNECTOR FOR ATTACHMENT TO A DRAIN TUBE

FIELD OF THE INVENTION

The present invention relates generally to medical equipment, and more particularly to medical equipment adapted for receipt or delivery of a fluid through a tube inserted through an orifice into the body of a patient.

BACKGROUND OF THE INVENTION

Typically, in a surgical procedure the distal end of a drain tube is placed at the surgical site in the patient's body. The proximal end of the drain tube extends out of the patient's body and is detachably connected to a suction/collection device. Thus, if fluids accumulate at the surgical site, the fluids may be removed through the drain tube.

A connector is generally attached to the proximal end of the drain tube. The connector includes an enlarged sleeve for slidably receiving a tube extending from the suction/collection device. Oftentimes the size of the connector and the size of the tube extending from the suction/collection device are not compatible. In these situations, an adapter is interposed between the connector and the tube extending from the suction/collection device to mate these two items in fluid communication.

Frequently, it is desirable to temporarily disconnect the drain tube from the suction/collection device, such as when the patient is moved. When the drain tube is disconnected from the suction/collection device, usually a plug is inserted into the connector.

There are two principal problems with the above-described procedure for using a drain tube that the present invention addresses. First, many times the adapter, and/or plug is misplaced and cannot be readily found when required. Second, drain tubes, the connectors attached thereto, and tubes extending from suction/collection devices vary in size. Thus, sometimes the correct size adapter and/or plug cannot be located. The present invention provides a solution for both of these problems.

SUMMARY OF THE INVENTION

The present invention provides a connector attachable to the proximal end of a drain tube for connecting the drain tube to a suction/collection device to provide drainage of fluids from a site within a patient. The connector includes a socket attachable to the proximal end of the drain tube so that the socket is in fluid flow communication with the drain tube.

An adapter having opposite ends is provided for connecting the socket to the suction/collection device. The adapter flexibly connects to the socket, and is also movable from a position having one end inserted in the socket, to a position with both ends removed from the socket.

A cap is provided for capping an end of the adapter, and for serving as a plug for insertion into the socket. The cap flexibly connects to the socket and is movable from a first position to a second position. In the first position, the cap receives the end of the adapter, while the end other end of the adapter is inserted in the socket, substantially sealing the end of the adapter. In the second position, the cap is removed from the end of the adapter.

The cap includes a tip, and a base opposite the tip. The base has a cross-sectional area greater than the cross-sectional area of the tip, wherein the cross-sectional area decreases in the direction towards the tip. This permits the tip to be inserted into the socket to function as a plug.

The adapter includes a section adapted for connection to the suction/collection device. The section includes a base and a tip. The base has a cross-sectional area greater than the tip, wherein the cross-sectional area decreases in the direction towards the tip. The advantage of this is that the adapter section can therefore be connected to tubes of many different sizes.

Both the adapter and the cap connect to the socket with flexible members. The flexible members are flexibly doubled over to use the cap and adapter. More particularly, the flexible member for the adapter is flexibly doubled over to insert one end of the adapter into the socket. Thereafter, the flexible member for the cap can be flexibly doubled over to place the cap over the opposite end of the adapter. The cap includes a recess which receives the end of the adapter, and substantially seals the end of the adapter. Thus, when one end of the adapter is inserted in the socket, and the cap covers the opposite end of the adapter, the socket is substantially sealed.

If the adapter is removed from the socket, the cap can be directly inserted into the socket. More particularly, the flexible member for the cap is twisted, and flexibly doubled over for inserting the tip of the cap into the socket, and thereby substantially sealing the socket. Tabs or grasping members extend from the cap and adapter to facilitate applying pulling or pushing forces to these items.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 illustrates a connector constructed in accordance with the present invention attached to the proximal end of a drain tube; and FIG. 2 illustrates an adapter from the connector of FIG. 1 inserted into one end of the connector.

DETAILED DESCRIPTION OF THE PREFERRED EMBODIMENT

Illustrated in FIG. 1 is a preferred embodiment of a connector 10 formed in accordance with the present invention. The connector 10 includes a hollow sleeve, or socket 14 attached to the proximal end of a drain tube 12. The socket 14 is generally frusto-conical in shape, having a base 18 at one end that narrows to a smaller diameter tip 20 at the opposite end. Preferably, the tip 20 connects to the drain tube 12.

In the preferred embodiment, the connector 10 is formed separately from the drain tube 12. In this regard, the diameter of the tip 20 is preferably sized to coaxially surround the outer circumference of the drain tube 12. In alternate embodiments, the tip 20 may be sized for slidable insertion into the end of the drain tube 12, sized to be generally the same diameter as the drain tube for an abutting, rather than an overlapping connection, or may be formed integrally with the drain tube. With all of these embodiments, the result is a path of fluid communication extending from the tube 12 through the socket 14.

Preferably, the connector 10 is composed of a polymer material, such as plastic, which is the same material used to form most drain tubes. The socket 14 may be attached to the drain tube 12 by any method that serves to substantially seal the circumference of the tip 20 to the circumference of the drain tube 12. In the preferred embodiment, a radial compression force is applied to the outer circumference of the tip 20, along with heat, to heat seal the tip 20 to the drain tube 12. Other methods may he used as well, such as ultrasonic or electronic welding, adhesives, and etc.

A generally frusto-conically shaped cap 22 is connected to the socket 14. The cap 22 includes a distal tip 23 that widens to a larger diameter base 24. A generally frusto-conically shaped recess 25 extends concentrically downward from the base 24 towards the tip 23. The recess 25 does not extend through the tip 23. Rather, the tip 23 seals the end of the recess 25.

A generally rectangularly-shaped flexible member 26 connects the cap 22 to the socket 14. The flexible member 26 extends radially from the base 18 of the socket 14. Ideally, the end 32 of the flexible member 26 attaches to the base 18 of the socket 14 a short distance below the rim 34 of the base, such that the rim extends above the surface of the flexible member. Ideally, the width of the flexible member 26 is greater than the radius of the base 24 of the cap 22, but less than the diameter of the base of the cap. The reason for this is so that the flexible member 26 will be narrower enough in width so that a second flexible member (as described below) can be also be connected to the socket 14.

The flexible member 26 includes an enlarged, annular circular section 28 having an inner diameter approximately equal to the inner diameter of the base 24 of the cap 22. The central axis of the annular circular section 28 lies substantially along the longitudinal centerline of the flexible member 26. The base 24 of the cap 22 extends from around the circumference of the annular circular section 28. Thus, the central axis of the cap 22 generally aligns with the central axis of the annular circular section 28, through which the recess 25 in the cap is exposed to the environment. The outer periphery of the annular circular section 28 circularly flares out beyond the outer periphery of the base 24 of the cap 22 to define a lip 30.

The cap 22 is not located at the distal end of the flexible member 26. Rather, the flexible member 26 extends beyond the cap 22 to form a tab or grasping member 36. However, the cap 22 is located closer to the distal end of the flexible member 26, than it is to the socket 14.

The connector 10 also includes an adapter 38 connected to the socket 14. The adapter 38 comprises two sections 40 and 42 that are both generally frusto-conical in shape. A central passageway 43 and 45 for fluid communication is formed generally axially through the sections 40 and 42. The sections 40 and 42 each respectively include a base 44 and 46 that narrows to form a tip 48 and respectively, at the opposite ends of each section. Preferably, the sections 40 and 42 are substantially identical in size and/or shape to one another, but in alternate embodiments they may differ in size and/or shape from each other. The bases 44 and 46 of the sections 40 and 42 are attached to one another and substantially coaxially aligned with each other.

A second flexible member 54 attaches the adapter 38 to the socket 14. The second flexible member 54 is generally rectangular in shape. The second flexible member 54 includes an enlarged circular portion 56 generally coaxially surrounding the bases 44 and 46 of the two adapter sections 40 and 42. Ideally, the width of the second flexible member 54 is greater than the radius of the base 44 or 46 of the two adapter sections 40 and 42, but loss than the diameter of the bases. The reason for this is so that the second flexible member 54 will be narrow enough in width to attach to the socket 14, along with the first flexible member 26. The adapter 38 passes centrally through the enlarged circular portion 56, which attaches to the bases 44 and 46 of each of the adapter sections 40 and 42. The enlarged circular portion 56 circularly flares out from the bases 44 and 46 of the two adapter sections 40 and 42 and defines an annular lip 58 around the adapter 38.

The flexible member 54 extends radially from the base 18 of the socket 14, opposite the first flexible member 26. Ideally, the end 60 of the second flexible member 54 attaches to the socket 14 at the same elevation as the first flexible member 26. Thus, the rim 34 of the socket 14 extends above the surface of the second flexible member 54.

The adapter 38 is not located at the distal end of the flexible member 54. Rather, the flexible member 54 extends beyond the adapter 38 to form a tab or grasping member 62. However, the adapter 38 is located closer to the distal end of the flexible member 54, than it is to the socket 14.

The second flexible member 54 permits the adapter 38 to be moved into and out of engagement with the socket 14. The flexible member 54 is flexibly doubled over itself to snugly insert one end of the adapter 38 into the socket 14.

When one end of the adapter 38 is inserted into the socket 14, the other flexible member 26 can be flexibly doubled over to fit the cap 22 over the other end of the adapter. More particularly, the recess 25 in the cap 22 snugly receives the end of the adapter 38, thereby sealing the end of the adapter and thereby substantially sealing the proximal end of the drain tube 12. Additionally, the flexible member 26 can be twisted and doubled over to insert the tip 23 of the cap 22 directly into the socket 14. When the tip 23 of the cap 22 is inserted into the socket 14, the cap snugly fits into the socket 14. This substantially seals the socket and closes off the proximal end of the drain tube 12 without use of the adapter 38. Thus, the cap 22 can also function as a plug for the adapter.

The annular lip 54 around the adapter 38 serves to facilitate removing the adapter 38 from the socket 14. More particularly, when the adapter 38 inserts into the socket 14, lip 54 abuts the rim 34 of the socket. A fiat object, such as a knife blade, can be slid between the lip 54 and the rim 34 and used to lever the adapter 38 out of the socket 14. Moreover, the lip 54 facilitates grasping for applying a pulling or pushing force to the adapter 38 for insertion and removal of the adapter to and from the socket 14. Further, the tab, or grasping member 62 of the adapter 38 also acts as a finger grip to facilitate insertion and removal of the adapter 38 to and from the socket 14. Additionally, the lip 54 serves as a stop to limit the depth the adapter 38 may be inserted into the socket 14.

The lip 30 extending from around the circumference of the base 24 of the cap 22 serves substantially similar functions. Namely, when the cap 22 is inserted into the socket 14, the annular lip 30 of the cap abuts the rim 34 of the socket 14. A fiat object, such as a knife blade, can be slid between the lip 30 and the rim 34 and used to lever the cap 22 out of the socket 14. The lip 30 also facilitates grasping for applying a pulling or pushing force to the cap 22. This aids in applying the cap 22 to, and removing the cap from the end of the adapter 38. It also aids in inserting and removing the cap 22 in and from the socket 14. The tab, or grasping member 36 extending beyond the cap 22 additionally serves as a finger grip. This facilitates application and removal of the cap 22 to and from the adapter 38, and insertion and removal of the cap in and from the socket 14. Further, the lip 30 serves as a stop for limiting the depth the cap 22 can be inserted into the socket 14, when the cap functions as a plug for the socket.

As described previously, each section 40 and 42 of the adapter 38 is generally frusto-conical in shape, with the narrower tip 48 and 50 of each section extending transversely away from the flexible member 54. The advantage of this is that the adapter 38 can connect the socket 14 with many different sizes of tubes that may extend from a suction/collection device. More particularly, the adapter 38 can be used with tubes having an inside diameter ranging from slightly greater than the diameter of the tip 50, up to tubes having an inside diameter nearly as large as the diameter of the base 46. When such a tube is slid over the narrower tip 50 of the adapter 38 towards the base 46, the diameter of the adapter increases. Eventually, the tube is slid far enough over the tip 50 that a diameter is reached which forms a seal between the tube and the adapter 38.

In alternate embodiments adapter sections 42 and 40 may include reverse barbs or ferrules (not shown). The barbs or ferrules serve to maintain adapter 38 in an insertion position when the adapter is inserted into a tube.

The cap 22 is also generally frusto-conical in shape, and therefore, can be used with tubes of many different sizes. The cap 22 may include both internal and external reverse barbs or ferrules (not shown).

Another advantage of the connector 10 is that cap 22 and adapter 38 are both attached thereto so that these items do not become separated from the connector and misplaced. Further, the system of attachment is such that the cap 22 and adapter 38 can be used while attached to the connector 10. That is, the cap 22 and adapter 38 do not have to be de-attached from the connector 10 to be used.

The different elements forming the connector 10 may be made separately and attached together. Alternatively, the connector may be made of integral one-piece construction or some elements may be made integrally with one another, and attached to other elements to form the connector 10. Preferably, as much as possible, the elements forming the connector are made of integral one-piece construction to minimize manufacturing costs.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A connector attachable to the proximal end of a drain tube for connecting the drain tube to a suction/collection device to provide drainage of fluids from a site within a patient, the connector comprising:
   (a) a socket having a central passageway and having a first end for connecting to the proximal end of the drain tube so that the socket is in fluid flow communication with the drain tube and having a second end opposite the first end;
   (b) an adapter for connecting the socket to the suction/ collection device, said adapter having a central passageway for fluid communication, said adapter being flexibly connected to the socket, said adapter further comprising a first section and a second section, wherein the first section and the second section each has a base and a tip, wherein the base of the first section is connected to the base of the second section, and wherein the base of each section has a cross sectional area greater than the cross-sectional area of the tip of each section, the cross-sectional area decreasing in the direction towards the tip, said adapter being movable from a first position to a second position, wherein in the first position the tip of the first section of the adapter is inserted into the second end of the socket, and in the second position the adapter is removed from the socket; and
   (c) a cap having a recess for receiving the second section of the adapter, said cap being flexibly connected to the socket, and movable from a first position to a second position to a third position, wherein in the first position the cap engages over the tip of the second section of the adapter to substantially seal the end of the adapter, in the second position the cap is removed from the tip of the second section of the adapter, and in the third position the cap is inserted into the second end of the socket.

2. The connector of claim 1, wherein the cap includes a tip and a base opposite the tip, the base having a cross-sectional area greater than the cross-sectional area of the tip, wherein the cross-sectional area decreases in the direction towards the tip to permit the cap to be inserted into the socket and function as a plug when the cap is in the third position.

3. The connector of claim 2, further comprising an annular lip radially extending from around the base of the cap.

4. The connector of claim 3, wherein the socket includes an open, distal end for insertion of the cap, the distal end having an annular, peripheral rim for abutting the annular lip of the cap when the cap is inserted into the socket for use as a plug.

5. The connector of claim 1, further comprising a flexible member connecting the cap to the socket and wherein the socket including a first end to which the flexible member is attached and a second end opposite the first end attachable to the proximal end of the drain tube.

6. The connector of claim 1, wherein the recess of the cap is frusto-conically shaped.

7. The connector of claim 1, wherein the cap has a base end and a distal tip, and wherein the recess for receiving the tip of the second section of the adapter is formed in the base end of the cap.

8. The connector of claim 7, wherein a flexible member connects the cap to the socket, the flexible member being connected to the base of the cap.

9. The cinnector of claim 1, wherein:
   (a) the first section of the adapter inserted into the socket when the adapter is in the first position, and the second section is for connection to the suction/collection device; and
   (b) a flexible member connecting the adapter to the socket.

10. The connector of claim 1, wherein the socket includes an open, distal end for insertion of the first section of the adapter into the socket, the distal end having an annular, peripheral rim to act as a stop for limiting insertion depth into the socket.

11. The connector of claim 1, further comprising an annular lip radially extending from around the base of the first section of the adapter.

12. The connector of claim 1, wherein the adapter first and second sections are generally axially aligned with one another.

13. The connector of claim 1, wherein a path of fluid communication is defined axially through the first and second sections of the adapter.

* * * * *

UNITED STATES PATENT AND TRADEMARK OFFICE
CERTIFICATE OF CORRECTION

PATENT NO. : 5,674,209  
DATED : October 7, 1997  
INVENTOR(S) : R.J. Yarger

Page 1 of 2

It is certified that error appears in the above-identified patent and that said Letters Patent is hereby corrected as shown below:

| COLUMN | LINE | |
|---|---|---|
| 3 | 4 | "he used" should read --be used-- |
| 3 | 50 | After "48 and" insert --50,-- |
| 3 | 64 | "loss than" should read --less than-- |
| 4 | 39 | "fiat" should read --flat-- |
| 4 | 54 | "fiat" should read --flat-- |
| 5 (Claim 1, | 63 line 18) | "cross sectional" should read --cross-sectional-- |
| 6 (Claim 9, | 44 line 1) | "cinnector" should read --connector-- |

UNITED STATES PATENT AND TRADEMARK OFFICE
CERTIFICATE OF CORRECTION

PATENT NO. : 5,674,209
DATED : October 7, 1997
INVENTOR(S) : R.J. Yarger

It is certified that error appears in the above-identified patent and that said Letters Patent is hereby corrected as shown below:

| COLUMN | LINE | |
|---|---|---|
| 6 (Claim 9, | 45 line 2) | "adapter inserted" should read --adapter is inserted-- |

Signed and Sealed this

Twenty-sixth Day of May, 1998

Attest:

BRUCE LEHMAN

Attesting Officer

Commissioner of Patents and Trademarks